(12) United States Patent
Bru-Magniez et al.

(10) Patent No.: US 6,420,468 B2
(45) Date of Patent: Jul. 16, 2002

(54) METHYLIDENE MALONATE NANOPARTICLES

(75) Inventors: Nicole Bru-Magniez, Paris; Xavier Guillon, Agen; Pascal Breton, Tigy; Patrick Couvreur, Villebon sur Yvette; François Lescure, Pechebusque; Claude Roques-Carmes, Besancon; Gérard Riess, Mulhouse, all of (FR)

(73) Assignee: Virsol, Paris (FR)

( * ) Notice: Subject to any disclaimer, the term of this patent is extended or adjusted under 35 U.S.C. 154(b) by 0 days.

(21) Appl. No.: 09/770,303

(22) Filed: Jan. 29, 2001

Related U.S. Application Data

(62) Division of application No. 09/284,455, filed on Apr. 16, 1999, now Pat. No. 6,211,273.

(51) Int. Cl.[7] ................................................ C08K 5/07
(52) U.S. Cl. ...................................... 524/365; 524/556
(58) Field of Search ................................. 524/365, 556

(56) References Cited

FOREIGN PATENT DOCUMENTS

FR WO 96/02278 * 2/1996

* cited by examiner

Primary Examiner—Edward J. Cain
(74) Attorney, Agent, or Firm—Dennison, Scheiner & Schultz

(57) ABSTRACT

Nanoparticles formed from a random polymer of at least one compound of formula (I)

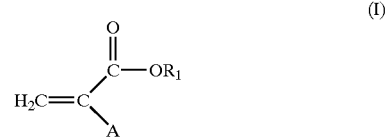

in which
A represents a

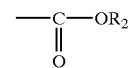

group or a

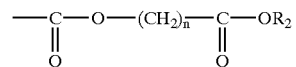

group;

$R_1$ and $R_2$, identical or different, represent a linear or branched $C_1$–$C_6$ alkyl group;

n=1, 2, 3, 4 or 5, having a diameter of less than 500 nm and an average molecular mass (Mw) between about 8000 and 100000, the nanoparticles being formed from homogeneous molecular species, and optionally containing a biologically active material.

24 Claims, 2 Drawing Sheets

METHYLIDENE MALONATE NANOPARTICLES

This application is a divisional of U.S. application Ser. No. 09/284,455 filed Apr. 16, 1999, now U.S. Pat. No. 6,211,273 which is the national stage of PCT FR97/01907 filed Oct. 24, 1997.

BACKGROUND OF THE INVENTION

The present invention relates to a novel method for the preparation of nanoparticles formed from a polymerised methylidene malonate compound, said nanoparticles, optionally containing one or more biologically active molecules, as well as to pharmaceutical compositions containing them.

"Nanoparticles" is understood as meaning sub-micron particles having a diameter of less than about 500 nanometers. Nanoparticles formed by emulsion polymerisation of an alkyl cyanoacrylate are described in the EP 0 007 895 patent. The method used in the preparation of these alkyl cyanoacrylate particles relies on the (anionic) polymerisation of the monomer which takes place spontaneously and in an aqueous medium. The preparation which follows the same principle (anionic emulsion polymerisation) of nanoparticles constituted of a methylidene malonate polymer is described notably in F. Lescure et al, Pharm. Res., 1994, 11, 1270–1276. These monomers, whose preparation is described in the EP 0 283 364 patent, have a structure close to that of the cyanoacrylates but the nitrile function of the latter is replaced with an ester or an ester ester. Like the cyanoacrylates, they polymerise in the cold in an aqueous medium and can be biodegradable.

However, the methylidene malonate nanoparticles thus obtained possess certain drawbacks.

In fact, the emulsion polymerisation of methylidene malonates in the form of nanoparticles leads, in aqueous phase and at slightly acid pH, to the formation of oligomers, mainly of the trimer or tetramer type, which are highly biodegradable. These molecular species are partially hydrosoluble, such that the dispersion of these nanoparticles in an aqueous medium leads to their solubilisation and to the rapid loss of the particle structure (P. Breton et al., Eur. J. Pharm. Biopharm., 1996, 42, 95–103). When a biologically active molecule is associated with the methylidene malonate nanoparticles, is therefore possible for the molecule to be released very rapidly after the administration, following the effect of dilution in the circulatory current which brings about the rapid solubilisation of the oligomers which form the particle matrix, before eventually arriving at the site of action of the active principle.

Certain experiments have shown that the polymerization at basic pH enabled the formation of polymers of higher molecular masses while maintaining the size of the nanoparticles. However, such syntheses are characterised by:

the impossibility of obtaining polymers of Mw<10 000, and a fortiori Mw<8000. constituting individualised nanoparticles, without forming aggregates and without the significant presence of oligomeric species.

the impossibility of constituting polymers of Mw>20 000 and a fortiori of higher Mw, at high pH (pH>7) without the inevitable formation of aggregates which render the intravascular administration of these preparations impossible.

"Mw" is understood as meaning the mass average molecular mass (or average molecular mass) defined as: $Mw = \Sigma ni.Mi^2 / \Sigma ni.Mi$ and Mp means the molecular mass of the quantitatively major species.

In the rest of the description, the molecular mass is expressed in polystyrene equivalents (Ep).

This preparative method is therefore not suitable if it is desired to prepare methylidene malonate nanoparticles constituted of:

polymers of average molecular mass between about 5000 and 10000, notably about 8000, polymers of average molecular mass greater than 20000, without forming aggregates.

SUMMARY OF THE INVENTION

The present invention therefore consists of the preparation of methylidene malonate nanoparticles having a diameter of less than 500 nm, in particular 100 to 500 nm. formed from homogeneous molecular species of wide-ranging masses (Mw between about 2000 and 80000). The principle consists in dissolving the monomer in a water-miscible aprotic organic phase but which, under the conditions of preparation of the nanoparticles, forms, with the aqueous polymerisation medium, a non-solvent mixture of the polymer formed.

"Aprotic organic phase" or "aprotic organic solvent", is understood as meaning an organic phase or a solvent without labile proton which is capable of initiating an anion.

The advantages of this preparative method according to the invention are numerous:

it enables a more homogeneous dispersion of the monomer in the polymerisation medium, it makes use of non-chlorinated solvents which are easy to evaporate since they are volatile, it prevents the formation of polymer aggregates, it gives rise to high polymerisation yields, it enables the constitution of polymers of homogeneous wide-ranging molecular mass (Mw about 2000 to 100000, notably about 2000 to 80000) in forming nanoparticles having a diameter of less than 500 nm.

Furthermore, the method enables the use of dispersing agents such as non-ionic surfactants or colloid protecting polymers, which leads to particles having flexible surface properties.

Finally, the molecular mass of the oligomers/polymers which form the nanoparticles according to the invention can be perfectly mastered by adjusting the following preparative conditions:

the monomer concentration in the organic phase, the pH and the molarity of the polymerisation medium, the nature and the concentration of the dispersing agent, the volume ratio of the aqueous phase (polymerisation medium)/organic phase, the mode of introduction of the organic mixture in the aqueous phase.

In a 1$^{st}$ aspect therefore, the invention relates to a method for the preparation of nanoparticles formed from a random polymer of at least one compound of formula (I)

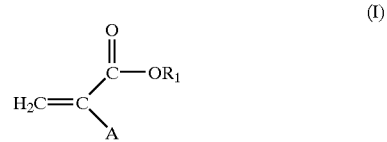

in which
A represents a

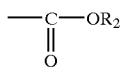

group or a

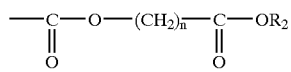

group;

$R_1$ and $R_2$, identical or different, represent a linear or branched $C_1$–$C_6$ alkyl group;

n=1, 2, 3, 4 or 5;

characterised in that the monomer(s) is (are), before the polymerisation, dissolved in a water-miscible aprotic organic solvent forming, with the polymerisation medium, a non-solvent mixture of the polymer formed.

In an advantageous aspect, the invention relates to a method for the preparation of nanoparticles formed from a polymer of a compound of formula (I)

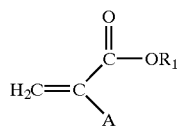

(I)

in which
A represents a

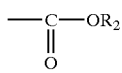

group or a

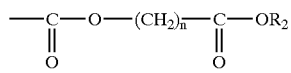

group;

$R_1$ and $R_2$, identical or different, represent a linear or branched $C_1$–$C_6$ alkyl group;

n=1, 2, 3, 4 or 5;

characterised in that before the polymerisation, the monomer is dissolved in a water-miscible aprotic organic solvent forming, with the polymerisation medium, a non-solvent mixture of the polymer formed.

According to a particular aspect, the method according to the invention enables the preparation of nanoparticles having a diameter of less than 500 nm, preferably between 100 and 500 nm. and an average molecular mass (Mw) between about 1000 and 100000, notably between about 1000 and 80000. in particular between about 2000 and 80000, preferably between about 8000 and 80000.

In particular, the method according to the invention comprises the steps consisting in:

preparing a solution of at least one compound of formula (I) in a water-miscible aprotic organic solvent.

adding, with stirring, this organic phase to an aqueous polymerisation medium at a pH between 4.5 and 10, recovering the nanoparticles thus obtained after homogenisation of the mixture and evaporating the organic solvent in vacuo.

The aqueous polymerisation medium can also be added to the organic phase which contains the monomer dissolved beforehand, and according to another aspect, the method according to the invention comprises the steps consisting in preparing a solution of at least one compound of formula (I) in a water-miscible aprotic organic solvent, adding, with stirring, to this organic phase, an aqueous polymerisation medium at a pH between 4.5 and 10, recovering the nanoparticles thus obtained after homogenisation of the mixture and evaporating the organic solvent in vacuo.

As illustrated later on in the Examples, the pH of the polymerisation medium is selected as a function of the molecular mass of the polymer that is desired to prepare.

Advantageously, the mixture of the organic phase and the aqueous medium is homogenised by continuous stirring for about 30 minutes and then, optionally, the preparation is completed by distilled water.

The polymer formed precipitates in the polymerisation medium and can be recovered by filtration for example. The nanoparticle suspension thus obtained can then be conditioned and lyophilised.

The aprotic organic solvent used for dispersing the monomer(s) must be a solvent of said monomer(s) which should also be miscible with water. This solvent is preferably selected from acetone, acetonitrile, dioxane and tetrahydrofuran, acetone being particularly preferred.

Preferred aspects of the method are the following:

the concentration of monomer(s) of formula (I) in the organic solvent is of the order 30 mg/ml to 150 mg/ml;

the molarity of the polymerisation medium is of the order of $\frac{1}{30}$ M to $\frac{1}{3}$ M;

volume ratio of the aqueous phase to the organic phase is between 3/1 and 20/1, preferably between 3/1 and 15/1.

Advantageously, the polymerisation medium contains one or more surfactants or colloid protectors.

The surfactants can be ionic or non-ionic surfactants for example. Non-ionic surfactants will preferably be used which are selected from copolymers of polyoxyethylene and polyoxypropylene, poloxamers and polysorbates. As colloid protector agents, polysaccharide derivatives will preferably be used, such as dextrans, hydrosoluble cellulose derivatives; polyethylene glycols; poly(vinyl alcohol).

Preferably, the compound polymerised to form the nanoparticles according to the method of the invention is a compound of formula (I) in which : A represents a

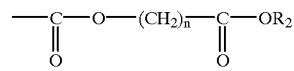

group, n=1 and $R_1$=$R_2$=ethyl.

In another preferred aspect, the compound polymerised to form the nanoparticles according to the method of the invention is a compound of formula (I) in which: A represents a

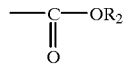

group, and $R_1=R_2=$propyl.

Advantageously, a mixture of compounds of formula (I) in which A is a

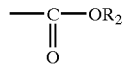

group or a

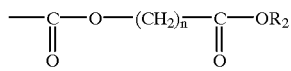

group as defined above, can also be random polymerised.

In a $2^{nd}$ aspect, the invention relates to the nanoparticles formed from a random polymer of at least one methylidene malonate compound of formula (I), having a diameter of less than 500 nm, preferably between 100 and 500 nm and an average molecular mass (Mw) between about 1000 and 100000, notably between 1000 and 80000, in particular between about 2000 and 80000, preferably between about 8000 and 80000, obtainable by this method.

In particular, said nanoparticles, obtainable by this method, are formed from a polymer of a compound of formula (I), have a diameter of less than 500 nm, preferably between 100 and 500 nm and an Mw between about 1000 and 80000, in particular between about 2000 and 80000, preferably between about 8000 and 80000.

In a preferred aspect, the invention relates to nanoparticles formed from a random polymer of at least one compound of formula (I), having a diameter of less than 500 nm. preferably between 100 and 500 nm and an average molecular mass (Mw) between about 8000 and 100000, preferably between about 8000 and 80000.

In particular, the invention relates to nanoparticles formed from a polymer of a compound of formula (I), having a diameter of less than 500 nm, preferably between 100 and 500 nm and an average molecular mass (Mw) between about 8000 and 80000.

Advantageously, said nanoparticles are formed from a compound of formula (I) in which A represents a

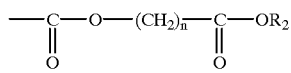

group, n=1 and $R_1=R_2=$ethyl.

In another preferred aspect, said nanoparticles are formed from a compound of formula (I) in which A represents a

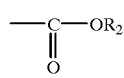

group and $R_1=R_2=$propyl.

Advantageously, said nanoparticles can be constituted of a random polymer of a mixture of compounds of formula (I) in which A is a

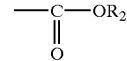

group or a

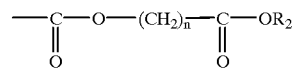

group as defined above.

According to a further aspect of the invention, said nanoparticles comprise, in their polymeric network, one or more biologically active molecules such as mentioned above.

In fact, in an advantageous aspect of the method according to the invention, the organic phase (when it is a biologically active molecule which is insoluble in water) or the polymerisation medium can contain one or more biologically active molecules.

"Biologically active molecule" is understood as meaning, in a non-limiting way, any molecule or macromolecule which has a prophylactic or curative biological activity, in vitro or in vivo, notably an anti-infectious agent, in particular an antiseptic agent, an antibiotic, an antiviral, an antiparasitic or antimitotic agent, notably an anticancer agent.

Antibiotic or antiseptic agents which can be used can be, for example, rifampicin and colistin.

As antiviral agents, didanosin, ribavirin, zidovudin, acyclovir, ganciclovir, foscarnet, vidarabin and zalcitabin can be cited in a non-limiting way.

Cis-plastin, 5-fluorouracil or taxol can, for example, be used as anti-cancer agents. Another advantageous antitumor agent is creatine phosphate whose activity is described in the application EP 0 614 366.

The invention also relates to pharmaceutical compositions containing said nanoparticles which comprise one or more biologically active molecules in association with a pharmaceutically acceptable vehicle.

The compositions according to the invention can be compositions which can be administered for example orally, sublingually, subcutaneously, intramuscularly, intravenously, transdermally, locally, rectally, via the pulmonary route, or nasally.

The suitable forms of administration notably comprise oral forms, such as tablets, gelatine capsules, powders, granules and oral solutions or suspensions, sublingual and buccal administration forms, as well as subcutaneous, intramuscular, intravenous, intranasal or intraocular and rectal administration forms.

DESCRIPTION OF THE PREFERRED EMBODIMENTS

The invention is illustrated by the Examples below, in which the preparation of the particles is carried out at ambient temperature (about 21° C.). The size, or diameter, of the nanoparticles was measured with a laser diffusion counter (Coulter Electronic Inc., USA). The molecular mass of the polymers was determined by gel permeation chromatography.

EXAMPLE 1

500 mg of 1-ethoxycarbonyl-1-ethoxycarbonylmethyleneoxycarbonylethene (Laboratoires UPSA/CARPIBEM, France), already desorbed of $SO_2$ for 3 hours under 25 mbars. are dissolved in 5.55 ml acetone. This solution is then mixed gradually and under magnetic stirring with 50 ml of an aqueous medium buffered at pH 8 ($Na_2HPO_4/KH_2PO_4$ 1/15 M) and containing 500 mg of dextran 70 (FLUKA CHEMIE, Switzerland). The almost instant polymerisation produces a cloudiness of the mixture which possesses a Tyndall effect characteristic of colloidal solutions. Stirring is maintained for 30 minutes after the complete introduction of the organic phase. Next. 50 ml of distilled water containing 2.5 g of glucose or trehalose (colloid protectors and cryoprotectors) are added to the nanoparticle suspension and the mixture is submitted to an evaporation in vacuo so as to remove the acetone and to reduce the volume of the aqueous suspension to 50 ml. After filtration on filter paper (pore diameter 5 to 15 µm), the preparation is lyophilised. As measured by laser diffusion, the particles contained in the filtrate have a diameter of 288 nm. The average molecular mass (Mw) of the methylidene malonate constituting the polymer matrix of the particles is evaluated to be 67000 by gel permeation chromatography.

EXAMPLE 2 pH Variation Study

The experiment is carried out following the technique described in Example 1, but only varying the pH only of the phosphate buffer. The results are given in Table 1 below, in which Mp is the molecular mass of the principal species and Mw is the average molecular mass of the polymer.

TABLE 1

| | pH of the polymerisation medium | | | | | | | |
|---|---|---|---|---|---|---|---|---|
| | 4.5 | 5.0 | 5.5 | 6.0 | 6.5 | 7.0 | 7.5 | 8.0 |
| size (nm) | 280 | 344 | 424 | 423 | 361 | 382 | 313 | 288 |
| standard deviation +/− nm | 9 | 9 | 7 | 6 | 9 | 7 | 2 | 3 |
| | characteristics of the polymer (Ep) | | | | | | | |
| Mp | 662 | 655 | 655 | 19700 | 31500 | 36900 | 40300 | 59300 |
| Mw | 2080 | 4740 | 11140 | 17600 | 28900 | 39000 | 53200 | 67200 |

The results show that the average molecular mass of the polymers which constitute the nanoparticles increase regularly with the pH of the polymerisation medium.

Figure 1:
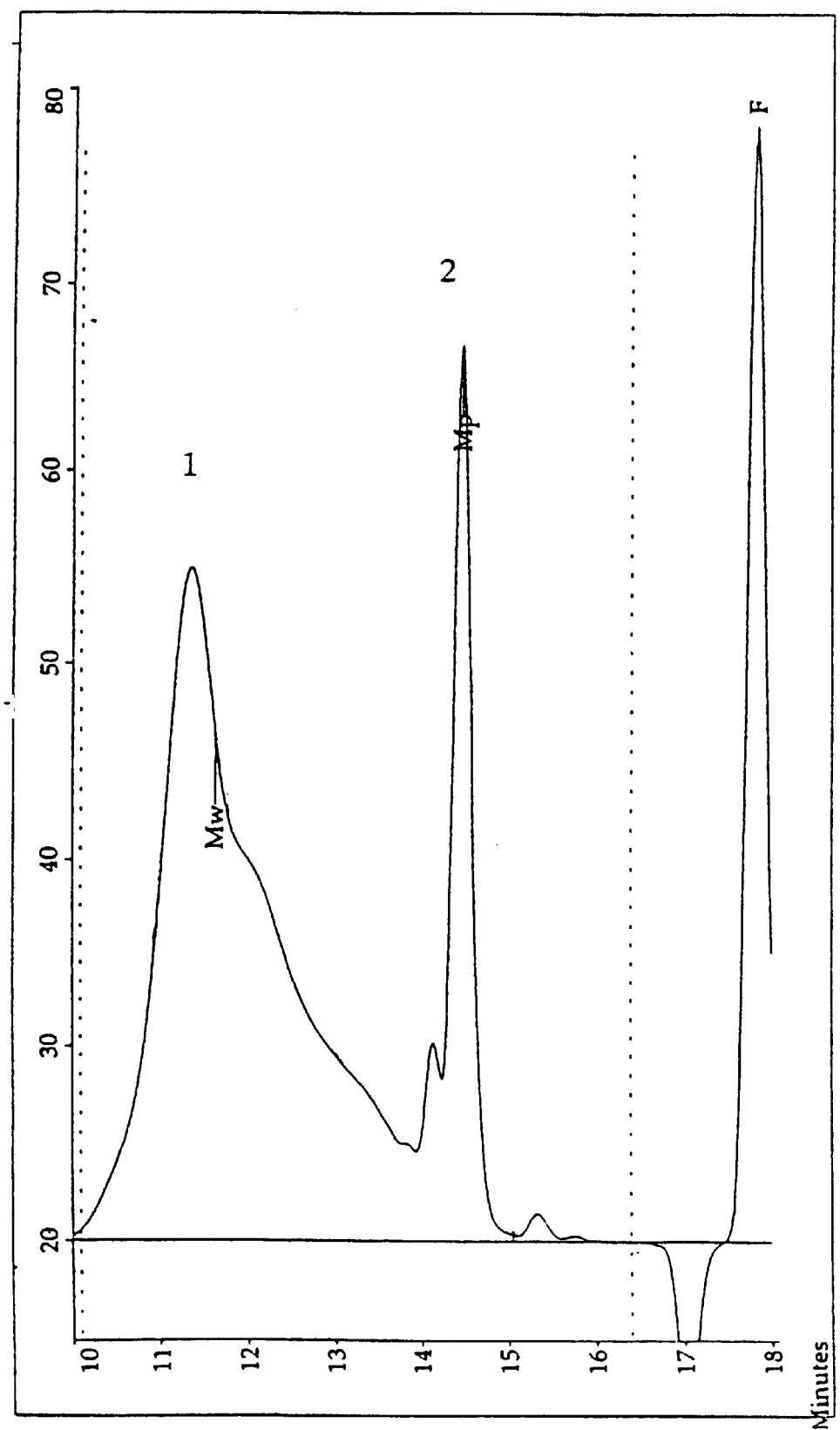
FIG. 1 is a gel permeation chromatographic profile of a polymer prepared according to the invention.

The gel permeation chromatographic profile of FIG. 1 represents the distribution of the molecular mass of the polymer prepared at pH 5.5 (concentration: 90 mg/ml). A broad peak is observed in 1 which corresponds to the species of high average molecular mass (Mw) and a narrow peak is observed in 2 which corresponds to the minor oligomers (major trimers and tetramers).

The dotted lines limit the analysable portion of the chromatogram. Peak F is that of toluene used as internal standard and the negative peak correspond to traces of water.

EXAMPLE 3

Study of the Variation of the Monomer Concentration

The experiment is carried out following the technique described in Example 1, but by varying only the monomer concentration in acetone. The results are given in Table 2 below:

TABLE 2

| | monomer concentration in the organic phase (mg/ml) | | |
|---|---|---|---|
| | 30 | 60 | 90 |
| size (nm) | 213 | 239 | 288 |
| standard deviation +/− nm | 2 | 4 | 3 |
| | characteristics of the polymer (Ep) | | |
| Mp | 31500 | 39600 | 59300 |
| Mw | 44700 | 63000 | 67200 |

The results show that the molecular mass of the principal species (Mp), as well as the average molecular mass (Mw) of the polymers which constitute the nanoparticles, increase regularly with the concentration of the monomer in the organic phase.

EXAMPLE 4

The experiment is carried out according to Examples 1 to 3 but in replacing dextran 70 colloid protector with a non-ionic surfactant, Pluronic F68 (BASF Corporation, USA).

The results are given in Table 3 below.

TABLE 3

| | pH of the polymerisation medium containing 0.5% Pluronic F 68 | | | | | | | |
|---|---|---|---|---|---|---|---|---|
| | 4.5 | 5.0 | 5.5 | 6.0 | 6.5 | 7.0 | 7.5 | 8.0 |
| Size (nm) | 87 | 80 | 95 | 117 | 122 | 121 | 146 | 153 |
| standard deviation +/− nm | 1 | 2 | 2 | 5 | 9 | 1 | 3 | 1 |
| | characteristics of the polymer (Ep)* | | | | | | | |
| Mp | 656 | 13300 | 14800 | 25600 | 38600 | 43700 | 45300 | 77800 |
| Mw | 5520 | 9740 | 12300 | 23600 | 33000 | 51600 | 70900 | 88900 |

*concentration of the monomer in acetone = 90 mg/ml.

The results show, for the same conditions of pH:

an increase in the molecular mass of the principal species (Mp) and in the average molecular mass (Mw) of the polymers constituting the nanoparticles in the presence of the surfactant with respect to the colloid protector, a decrease in the size of these same nanoparticles in the presence of the surfactant with respect to the colloid protector.

EXAMPLE 5

Study of the Molarity of the Polymerisation Medium

According to the method described in Example 1, 500 mg of monomer are dissolved in 16.6 ml acetone are introduced into a phosphate buffer ($Na_2HPO_4/KH_2PO_4$) of increasing molarity, and further containing 0.5% Pluronic F68.

The results are given in Table 4 below:

TABLE 4

| molarity | size of the nanoparticles (nm) | standard deviation (nm) | Mp (Ep) | Mw (Ep) |
|---|---|---|---|---|
| 0.033 M | 127 | 2 | 15200 | 12500 |
| 0.066 M | 123 | 1 | 14600 | 12400 |
| 0.133 M | 124 | 1 | 653 | 9790 |
| 0.267 M | 179 | 3 | 660 | 8690 |

The results show a decrease in the average molecular mass (Mw) of the polymers which constitute the nanoparticles in proportion to an increase in the molarity of the medium.

EXAMPLE 6

Nanoparticles are prepared according to Examples 1 to 3 and are compared to the nanoparticles prepared according to the method described by Lescure et al., Pharm. Res. 1994, 11, 1270–1276. For this. 100 mg of monomer are introduced with stirring in 10 ml of a phosphate buffer medium ($Na_2HPO_4/KH_2PO_4$ 1/15 M) of pH 5 to 8.
The results are given in Table 5 below in which the oligomers are defined as any molecular species of molecular mass less than or equal to 920.

TABLE 5

| | | pH of the polymerisation medium containing 1% dextran 70 | | | | | |
|---|---|---|---|---|---|---|---|
| | | 5.5 | 6.0 | 6.5 | 7.0 | 7.5 | 8.0 |
| Method according to Lescure et al., 1994 | size (nm) | 260 | 296 | 337 | 335 | 271 | 322 |
| | standard deviation +/− nm | 5 | 5 | 10 | 4 | 6 | 6 |
| | Mp | 666 | 660 | 675 | 685 | 15572 | 13000 |
| | Mw | 1719 | 2421 | 5335 | 6041* | 6759* | 7594* |
| | % oligomers | 43 | 53 | 27 | 38 | 18 | 13 |
| | yield of nanoparticles obtained % ±5 | 87 | 79.5 | 71.5 | 59.5 | 21 | 23 |
| Method according to the invention** | size (nm) | 424 | 423 | 361 | 382 | 313 | 288 |
| | standard deviation +/− nm | 7 | 6 | 9 | 7 | 2 | 3 |
| | Mp | 655 | 19695 | 31508 | 36290 | 40278 | 59300 |
| | Mw | 11138 | 17569 | 28918 | 38997 | 53181 | 67201 |

TABLE 5-continued

| | pH of the polymerisation medium containing 1% dextran 70 | | | | | |
|---|---|---|---|---|---|---|
| | 5.5 | 6.0 | 6.5 | 7.0 | 7.5 | 8.0 |
| % oligomers | 19 | 14 | 8 | 4 | 3 | 2 |
| yield of nanoparticles obtained % ±5 | 82.5 | 73 | 84.5 | 91 | 85 | 86.5 |

*presence of aggregates
**monomer concentration in acetone = 90 mg/ml

The results show that, for any experimental condition of identical pH:
- the average molecular mass (Mw) of the polymers constituting the nanoparticles prepared according to Lescure et al. is less than that of the polymer obtained according to the method of the invention;
- the contents of the oligomers (trimers-tetramers) constituting the polymers are significantly less for the nanoparticles prepared according to the method of the invention;
- the yields of polymerisation in the form of nanoparticles are higher for the method of the invention compared to the method according to Lescure et al (the formation of aggregates results in low yields at basic pH for the method according to Lescure et al.).

Figure 2:
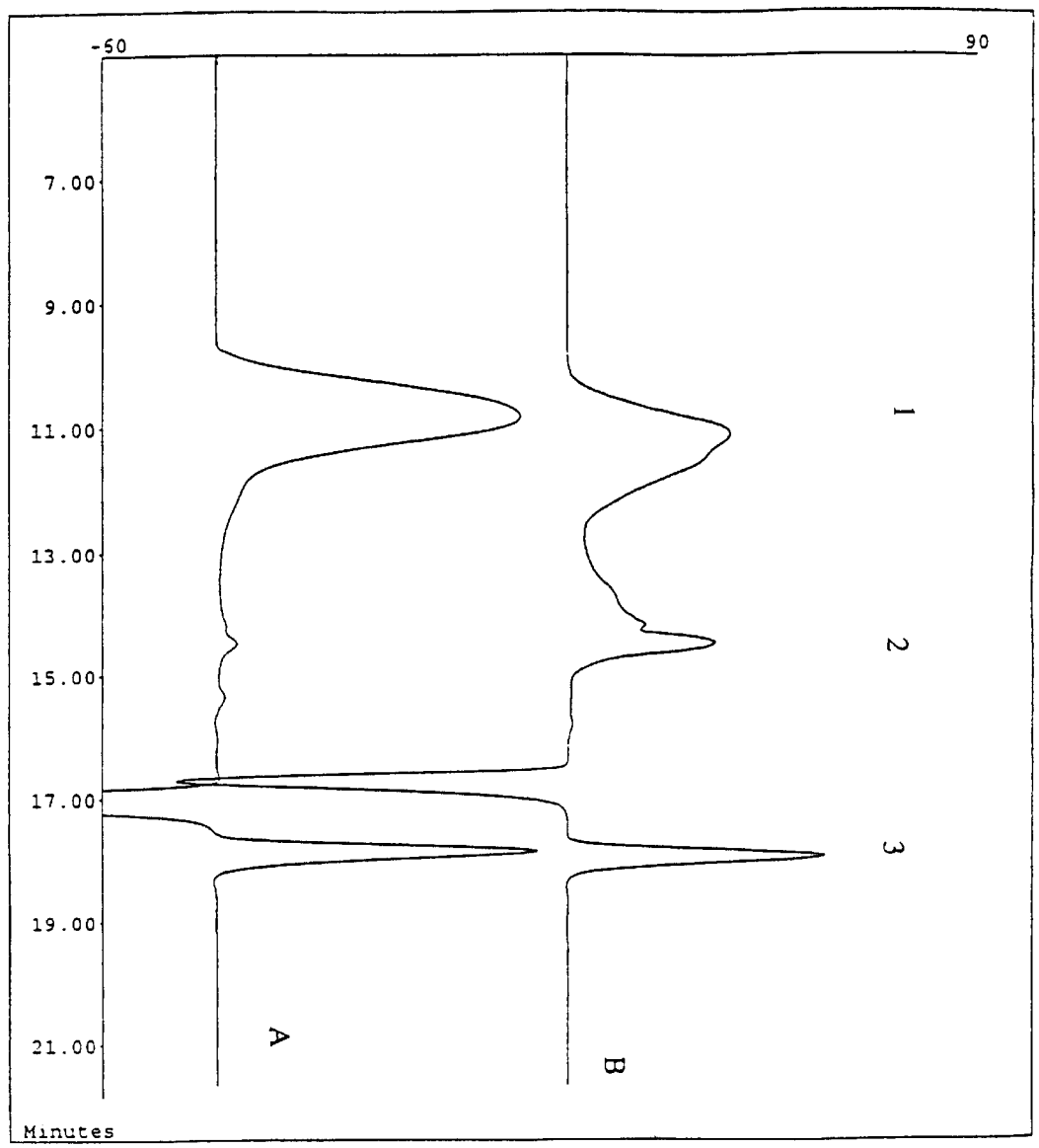
FIG. 2 is a gel permeation chromatographic profiled of another polymer prepared according to the invention and a comparative polymer.

The gel permeation chromatography profile of FIG. 2 represents the distributions of molecular mass of the polymers prepared at pH 7.5 according to the method of the invention on the one hand (trace A), and according to the method of Lescure et al on the other (trace B). Apart from peak 3 corresponding to toluene, for peak A, a single peak 1 is observed which corresponds to the principal species (Mp=40278) while for trace B, the presence of a significant peak 2 is observed also which corresponds to the oligomers (trimers and tetramers).

EXAMPLE 7

50 ml of an aqueous medium buffered at pH 5; 6.5 or 8 ($Na_2HPO_4/KH_2PO_4$ 1/15 M) and containing 0.5% of Pluronic F68 (BASF Corporation, USA) are added gradually and with magnetic stirring to 5.55 ml of a solution of 500 mg of 1-ethoxycarbonyl-1-ethoxycarbonylmethyleneoxycarbonylethene monomer (LABORATOIRES UPSA/ CARPIBEM, France), already desorbed of $SO_2$ for 3 hours under 25 mbars in 5.55 ml of acetone. The stirring is maintained for 16 hours for the tests at pH 5 and 6.5 or for 30 minutes for the test at pH 8 after the complete introduction of the organic phase. Next, 50 ml of distilled water containing 2.5 g of glucose or trehalose (colloid protectors and cryoprotectors) are added to the nanoparticle suspension and the mixture is submitted to evaporation in vacuo so as to remove the acetone and to reduce the volume of the aqueous suspension to 50 ml. After filtration on filter paper (pore diameter 5 to 15 μm), the preparation is lyophilised. The diameter of the particles contained in the filtrate is measured by laser diffusion. The average molecular mass (Mw) of the methylidene malonate constituting the polymer matrix of the particles is evaluated by gel permeation chromatography.

The results are given in Table 6 below, in which Mp is the molecular mass of the principal species and Mw is the average molecular mass of the polymer.

The yield is determined by the ratio of the amount of monomer introduced into the reaction medium and the amount of polymer constituting the nanoparticles.

TABLE 6

| | pH of the polymerisation medium | | |
|---|---|---|---|
| | 5.0 | 6.5 | 8.0 |
| size (nm) | 848 | 394 | 754 |
| standard deviation +/−nm | 36 | 32 | 34 |
| | characteristics of the polymer (Ep) | | |
| Mp | 312 | 24300 | 26500 |
| Mw | 6450 | 20100 | 20100 |
| | yield | | |
| % | 59 | 57 | 30 |
| standard deviation | 5.1 | 4.6 | 4.2 |

EXAMPLE 8

Use of Different Solvents

The experiment is carried out following the method of Example 1, but using acetone, acetonitrile or tetrahydrofuran (THF) as solvent of the monomer.

The results are given in Table 7 below.

TABLE 7

| Solvent | Average particle size (nm) | yield (%) | Mw |
|---|---|---|---|
| Acetone | 253 | 74 | 54 100 |
| Acetonitrile | 197 | 69 | 31 700 |
| THF | 191 | 70 | 30 300 |

EXAMPLE 9

Study of the Water/Solvent Volume Ratio

The experiment is carried out following the method of Example 1, but varying the water/acetone volume ratio.

The results are given in Table 8 below:

TABLE 8

| | Water/solvent volume ratio | | |
|---|---|---|---|
| | 4.5/1 | 9/1 | 18/1 |
| size (nm) | 241 | 288 | 334 |
| yield (%) | 74 | 74 | 85 |
| | characteristics of the polymer | | |
| Mp | 62100 | 59300 | 33100 |
| Mw | 42000 | 67200 | 24600 |

EXAMPLE 10

Implementation of the Method at pH 10.

The tests were carried out in an aqueous medium at pH=10 in the presence either of a surfactant or a colloid protector and this, either following the method of Example 1 or following the method of Example 7.

1) test 1

100 mg of 1-ethoxycarbonyl-1-ethoxycarbonylmethyleneoxycarbonyl-ethene monomer are dissolved in 1 ml of acetone.

This solution is then added gradually and with magnetic stirring into 10 ml of an aqueous medium at pH=10 and containing 100 mg of Dextran 70.

The polymerisation is instantaneous. The stirring is maintained for 30 minutes after the introduction of the whole of the organic phase. Next, 10 ml of distilled water are added to the nanoparticle suspension, and the mixture is submitted to an evaporation in vacuo so as to remove the acetone. The medium is then centrifuged (v=10 000 rpm. 10 min at 4° C.).

2) test 2

The experimental protocol is identical to that of test 1 but by replacing Dextran 70 with Pluronic F68.

3) test 3

10 ml of an aqueous medium at pH=10 containing 100 mg of Dextran 70 are added gradually with magnetic stirring into an organic phase constituted of 100 mg of monomer and 1 ml of acetone. The polymerisation is instantaneous. The stirring is maintained for 30 minutes after the introduction of the whole of the aqueous phase. Next, 10 ml of distilled water are added to the nanoparticle suspension and the mixture is submitted to an evaporation in vacuo so as to remove the acetone. The medium is then centrifuged (v=10 000 rpm. 10 min at 4° C.).

4) test 4

The experimental protocol is identical to that of test 3 but the Dextran 70 is replaced with Pluronic F68. After centrifugation, the nanoparticles contained in the plug are analysed by steric exclusion chromatography to determine their weight average molecular mass (Mw).

The results are given in the Table 9 below.

TABLE 9

| | Mw | Particle size (nm) |
|---|---|---|
| Test 1 | 8 800 | 240 |
| Test 2 | 6 900 | 245 |
| Test 3 | 1 400 | 316 |
| Test 4 | 1 850 | 333 |

EXAMPLE 11

The experiment is carried out following the polymerisation technique described in Example 1, but using 1,1-propoxycarbonylethene (Laboratoires UPSA/CARPIBEM, France) hereinafter referred to as MM 3.3 alone or in a mixture with the 1-ethoxycarbonyl-1-ethoxycarbonylmethyleneoxy-carbonylethene monomer (Laboratoires UPSA/CARPIBEM. France), hereinafter referred to as MM 2.1.2. The results are given in Table 10 below, in which Mp is the molecular mass of the principal species and Mw is the average molecular mass of the polymer.

TABLE 10

| | Ratio MM 3.3/MM 2.1.2 | | | |
|---|---|---|---|---|
| | 100/0 | 75/25 | 50/50 | 25/75 |
| Size | 123 | 223 | 298 | 155 |
| Yield (%) | 77 | 73 | 80 | 78 |
| | Characteristics of the polymer | | | |
| Mp | 44764 | 92090 | 37467 | 21727 |
| Mw | 44122 | 89793 | 37467 | 21727 |

EXAMPLE 12

Preparation of Nanoparticles Containing Rifampicin 5 mg of rifampicin base (Sigma) are dissolved in 1 ml of acetone to which 90 mg of 1-ethoxycarbonyl-1-ethoxycarbonyl methyleneoxy-carbonylethene monomer (LABORATOIRES UPSA/CARPIBEM. France) are added, beforehand desorbed of $SO_2$ for 3 hours under 25 mbars. With the aid of a glass pipette, this solution is then added gradually and with constant stirring (750 rpm) to 9 ml of aqueous medium buffered at pH 6.0 with the aid of a phosphate buffer ($Na_2HPO_4/KH_2PO_4$ 0.066 M) and containing 90 mg of dextran 70 (1% w/v). After 18 hours of polymerisation at 20° C., 9 ml of distilled water containing 5% of D-glucose are added with stirring to the nanoparticle suspension, the mixture is then submitted to an evaporation in vacuo with the aid of a Rotavapor (20° C., 25 mbars) so as to remove the acetone and to reduce the volume of the aqueous suspension to 9 ml. The preparation is then lyophilised: freezing takes place at −30° C. and sublimation at +20° C. for 36 hours at a pressure of 0.05 mbar.

The size of the nanoparticles and the rifampicin concentration are measured before and after lyophilisation. The size is measured by laser diffusion. The determination of the rifampicin is carried out by high performance liquid chromatography coupled to a spectrophotometer. The mobile phase is composed of a mixture of methanol/0.05 M ammonium acetate (65:35). the pH is adjusted to 7.3, the flow rate is fixed at 1 ml/min and the absorption is read at 254 nm. The content of rifampicin which is not bound to the nanoparticles is measured in the supernatant obtained after ultracentrifugation of the nanoparticle suspension (80000 g. 1 h at 4° C.). The amount of rifampicin bound to the nanoparticles corresponds to the fraction present in the plug, which is dissolved in THF before proceeding with the direct rifampicin determination.

The following results are obtained:

size of the nanoparticles containing rifampicin: 266±63 nm before lyophilisation and 282±54 nm after lyophilisation;

percentage binding of rifampicin : 8.5±0.5% before and after lyophilisation.

EXAMPLE 13

Preparation of Nanoparticles Containing Colistin

The experiment is carried out in the same way as in Example 12, but the active principle being hydrosoluble, it is incorporated in the polymerisation medium at a concentration of 0.5 mg/ml before addition of the organic phase. The size of the nanoparticles containing colistin measured by laser diffusion is 282±65 nm after evaporation and 283±26 nm after conservation at +4° C. for 4 days. Determined according to the gelose diffusion technique (S. P. Gotoff et al., Antimicrob. Agents Chemother, 1962, 107–113), colistin is found at the concentration of 15 µg/ml in the supernatant obtained after ultracentrifugation of the nanoparticle suspension (80000 g, 1 hour at 4° C.): the fraction which is not bound to the nanoparticles is then evaluated at 3% of the total amount of colistin added.

EXAMPLE 14

Preparation of Nanoparticles Containing Azidothymidine (AZT) (Sigma Aldrich Chimie, France)

240 mg of 1-ethoxycarbonyl-1-ethoxycarbonylmethyleneoxycarbonylethene monomer (Laboratoires UPSA/CARPIBEM. France), already desorbed of $SO_2$ for 3 hours under 25 mbars, are dissolved in 2.5 ml acetone. With the aid of a propipette, this solution is then gradually added and with constant stirring to 22.5 ml of aqueous medium buffered at pH 8.0 with the aid of a phosphate buffer ($Na_2HPO_4/KH_2PO_4$ 0.066 M) and containing 225 mg of dextran 70 (1% w/v), as well as the hydrosoluble active principle at a concentration of 0.53 mg/ml. After 18 hours' polymerisation at 20° C., 22.5 ml of demineralised water containing 5% of D-glucose are added with stirring to the nanoparticle suspension, the mixture is then submitted to an evaporation in vacuo with the aid of a Rotavapor (20° C., 25 mbars) so as to remove the acetone and to reduce the volume of the aqueous suspension to 39.0 ml. The preparation is then lyophilised; freezing takes place at −30° C. and sublimation at +20° C. for 36 hours at a pressure of 0.05 mbar.

The size of the nanoparticles containing AZT measured by laser diffusion is 255±63 nm before lyophilisation. The content of AZT in the supernatant after centrifugation of the nanoparticle suspension (12000 rpm, 1 hour at 4° C.) is determined by UV spectrophotometry at 266 nm. A concentration of 98 µg/ml is obtained: the fraction which is not bound to the nanoparticles is therefore evaluated to be 31.9% of the total amount of AZT added. The fraction of AZT bound to the nanoparticles is therefore 68.1%.

EXAMPLE 15

Preparation of Nanoparticles Containing Creatine Phosphate (Boehringer Mannheim)

The encapsulation of creatine phosphate is carried out according to the technique of Example 14. The size of the nanoparticles containing creatine phosphate measured by laser diffusion is 275±260 nm before lyophilisation. The determination of the creatine phosphate is carried out by high performance liquid chromatography coupled to a spectrophotometer. The mobile phase is composed of a phosphate buffer ($KH_2PO_4$ 0.05 M) adjusted to pH 3.3. The flow rate is fixed at 2 ml/min and the absorption is read at 200 nm.

The content of creatine phosphate which is not bound to the nanoparticles is measured in the supernatant obtained after centrifugation of the nanoparticle suspension (12000 rpm, 1 hour at 4° C.). The creatine phosphate is found at a concentration of 463 µg/ml in the supernatant: the fraction which is not bound to the nanoparticles is therefore evaluated at 81% of the total amount of creatine phosphate added. The fraction of creatine phosphate bound to the nanoparticles is therefore 19%.

EXAMPLE 16

Preparation of Nanoparticles Containing 5-fluorouracile (5-FU)

The encapsulation of 5-FU (Sigma Aldrich Chimie, France) is carried out according to the technique of Example 14. The size of the nanoparticles containing the 5-FU measured by laser diffusion is 516±88 nm before lyophilisation. Determined by UV spectrophotometry at 266 nm, the 5-FU is found at a concentration of 70 µg/ml in the supernatant obtained after centrifugation of the nanoparticle suspension (12 000 rpm, 1 hour at 4° C.): the fraction which is not bound to the nanoparticles is therefore evaluated at 23.3% of the total amount of 5-FU added. The fraction of 5-FU bound to the nanoparticles is therefore 76.7%.

What is claimed is:

1. Nanoparticles formed from a random polymer of at least one compound of formula (I)

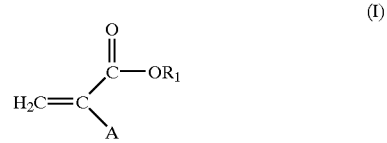

in which

A represents a

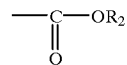

group or a

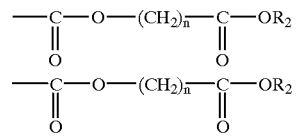

group;

$R_1$ and $R_2$, identical or different, represent a linear or branched $C_1$–$C_6$ alkyl group;

n=1, 2, 3, 4 or 5, having a diameter of less than 500 nm and an average molecular mass (Mw) between about 8000 and 100000, said nanoparticles being formed from homogeneous molecular species.

2. Nanoparticles formed from a polymer of formula (I)

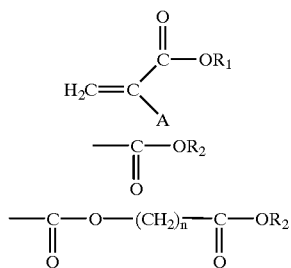

in which

A represents a

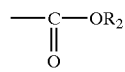

group or a

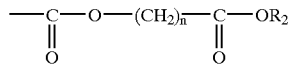

group;

$R_1$ and $R_2$, identical or different, represent a linear or branched $C_1$–$C_6$ alkyl group;

n=1, 2, 3, 4 or 5, having a diameter of less than 500 nm and an average molecular mass (Mw) between about 8000 and 100000, said nanoparticles being formed from homogeneous molecular species.

3. The nanoparticles according to claim 1, formed from a polymer of a compound of formula (I) in which A is a

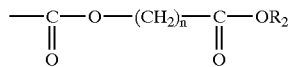

group, n=1, $R_1$=$R_2$=ethyl.

4. The nanoparticles according to claim 1, characterised in that they comprise one or more biologically active molecules.

5. Pharmaceutical composition containing nanoparticles according to claim 4 as active principle in association with a pharmaceutically acceptable vehicle.

6. The nanoparticles according to claim 1, having a diameter of between 100 and 500 nm.

7. The nanoparticles according to claim 1, having an average molecular mass (Mw) between about 8000 and 80000.

8. The nanoparticles according to claim 2, having a diameter of between 100 and 500 nm.

9. The nanoparticles according to claim 2, having an average molecular mass (Mw) between about 8000 and 80000.

10. Nanoparticles formed from a random polymer of at least one compound of formula (I)

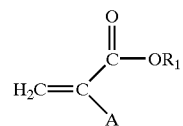

in which

A represents a

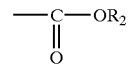

group or a

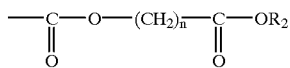

group;

$R_1$ and $R_2$, identical or different, represent a linear or branched $C_1$–$C_6$ alkyl group;

n=1, 2, 3, 4 or 5, having a diameter of less than 500 nm and an average molecular mass (Mw) between about 8000 and 100000, said nanoparticles being formed from homogeneous molecular species and obtained by a method comprising the steps of dissolving said at least one compound of formula (I) in a water-miscible aprotic organic solvent, and mixing the dissolved at least one compound of formula (I) with an aqueous polymerization medium, resulting in a non-solvent mixture of the polymer formed.

11. Nanoparticles according to claim 10, wherein:

the step of dissolving forms an organic phase;

said mixing comprises adding to said organic phase, said aqueous polymerization medium at a pH between 4.5 and 10 to form a mixture; and nanoparticles are recovered from the non-solvent mixture by homogenizing and evaporating the solvent in vacuo.

12. Nanoparticles according to claim 10, wherein:

the step of dissolving forms an organic phase;

said mixing comprises adding said organic phase to said aqueous polymerization medium at a pH between 4.5 and 10 to form a mixture; and recovering the nanoparticles obtained thereby after homogenizing the mixture and evaporating the organic solvent in vacuo.

13. Nanoparticles according to claim 12, wherein the aprotic organic solvent is selected from the group consisting of acetone, acetonitrile, dioxane and tetrahydrofuran.

14. Nanoparticles according to claim 12, wherein said at least one compound of formula (I) is present in the organic solvent in a concentration of about 30 mg/ml to 150 mg/ml.

15. Nanoparticles according to claim 12, wherein the polymerization medium has a molarity of about 1/30 M to 1/3 M.

16. Nanoparticles according to claim 12, wherein the polymerization medium contains at least one surfactant or colloid protectors.

17. Nanoparticles according to claim 16, wherein the at least one surfactant is a non-ionic surfactant selected from the group consisting of copolymers of polyoxyethylene and polyoxypropylene, poloxamers and polysorbates.

18. Nanoparticles according to claim 16, wherein the at least one colloid protector is selected from the group consisting of dextrans, hydrosoluble cellulose derivatives, polyethylene glycols and poly(vinyl alcohol).

19. Nanoparticles according to claim 12, wherein the organic phase or the polymerization medium contains at least one biologically active molecule.

20. Nanoparticles according to claim 17, wherein the at least one colloid protector is selected from the group consisting of dextrans, hydrosoluble cellulose derivatives polyethylene glycols and poly(vinyl alcohol).

21. Nanoparticles according to claim 16, wherein the organic phase or the polymerization medium contains at least one biologically active molecule.

22. Nanoparticles according to claim 12, wherein the polymerized compound is a compound of formula (I) in which A represents a group of formula:

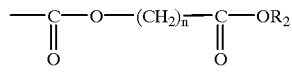

in which $R_1=R_2=$ethyl, and $n=1$.

23. Nanoparticles according to claim 10, wherein the polymerized compound is a compound of formula (I) in which A represents a group of formula:

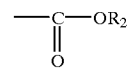

and $R_1=R_2=$propyl.

24. Nanoparticles according to claim 8, wherein a mixture of compounds of formula (I) in which A is a

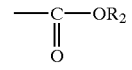

group or a

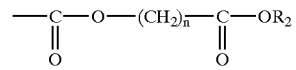

group, is randomly polymerized.

* * * * *